US012389941B2

(12) United States Patent
Deng et al.

(10) Patent No.: US 12,389,941 B2
(45) Date of Patent: Aug. 19, 2025

(54) ELECTRONIC ATOMIZATION DEVICE AND ATOMIZER THEREOF

(71) Applicant: SHENZHEN SMOORE TECHNOLOGY LIMITED, Shenzhen (CN)

(72) Inventors: Changwei Deng, Shenzhen (CN); Weiguang Hu, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 680 days.

(21) Appl. No.: 17/421,445

(22) PCT Filed: Oct. 15, 2020

(86) PCT No.: PCT/CN2020/121010
§ 371 (c)(1),
(2) Date: Jul. 8, 2021

(87) PCT Pub. No.: WO2021/073552
PCT Pub. Date: Apr. 22, 2021

(65) Prior Publication Data
US 2022/0071282 A1    Mar. 10, 2022

(30) Foreign Application Priority Data
Oct. 18, 2019    (CN) .......................... 201910996274.3

(51) Int. Cl.
*A24F 40/42*    (2020.01)
*A24F 40/10*    (2020.01)
(Continued)

(52) U.S. Cl.
CPC .............. *A24F 40/42* (2020.01); *A24F 40/10* (2020.01); *A24F 40/485* (2020.01);
(Continued)

(58) Field of Classification Search
None
See application file for complete search history.

(56) References Cited

U.S. PATENT DOCUMENTS

2015/0027470 A1* 1/2015 Kane ..................... A24F 40/485
131/328
2015/0282528 A1* 10/2015 Liu ....................... A24F 40/485
131/329
(Continued)

FOREIGN PATENT DOCUMENTS

CN    203388271 U   *   1/2014
CN    204351070 U      5/2015
(Continued)

OTHER PUBLICATIONS

English language machine translation of Qiu et al. CN-208837096-U, 2019.*
(Continued)

*Primary Examiner* — Manley L Cummins, IV
(74) *Attorney, Agent, or Firm* — Ballard Spahr LLP

(57) ABSTRACT

An electronic atomizing device and an atomizer thereof are provided. The atomizer includes a liquid storage assembly and an atomizing assembly. The liquid storage assembly forms a liquid storage cavity therein and an accommodating cavity in communication with the liquid storage cavity, the accommodating cavity includes a first opening formed on a surface of the liquid storage assembly. The atomizing assembly is detachably embedded in the liquid storage assembly via the first opening and the atomizing assembly is accommodated in the accommodating cavity in an interference fit manner via at least one sealing member.

18 Claims, 8 Drawing Sheets

(51) Int. Cl.
*A24F 40/485* (2020.01)
*A61M 11/04* (2006.01)
(52) U.S. Cl.
CPC ... *A61M 11/042* (2014.02); *A61M 2205/0233* (2013.01); *A61M 2205/8206* (2013.01)

(56) References Cited

U.S. PATENT DOCUMENTS

| | | | | |
|---|---|---|---|---|
| 2015/0342258 | A1* | 12/2015 | Chen | A24F 40/44 131/329 |
| 2017/0325503 | A1 | 11/2017 | Liu | |
| 2018/0007961 | A1* | 1/2018 | Zhu | A24F 40/485 |
| 2018/0263294 | A1 | 9/2018 | Qiu | |
| 2021/0112858 | A1* | 4/2021 | Liu | A24F 40/485 |

FOREIGN PATENT DOCUMENTS

| | | | |
|---|---|---|---|
| CN | 205848691 U | | 1/2017 |
| CN | 107072304 A | | 8/2017 |
| CN | 207428418 U | * | 6/2018 |
| CN | 207428419 U | | 6/2018 |
| CN | 207678853 U | | 8/2018 |
| CN | 208318232 U | | 1/2019 |
| CN | 208657987 U | | 3/2019 |
| CN | 208837096 U | | 5/2019 |
| CN | 208863596 U | | 5/2019 |
| CN | 109998173 A | | 7/2019 |
| CN | 110613175 A | | 12/2019 |
| CN | 209788494 U | | 12/2019 |
| CN | 110693087 A | | 1/2020 |
| CN | 211129742 U | | 7/2020 |
| EP | 3381304 A1 | | 10/2018 |
| KR | 101820827 B1 | | 1/2018 |
| WO | 2016029471 A1 | | 3/2016 |
| WO | 2017070871 A1 | | 5/2017 |

OTHER PUBLICATIONS

CN 207428418U, Atomization device and electronic cigarette thereof, (Year: 2018).*
CN208837096u, Cigarette cartridge and electronic cigarette, (Year: 2019).*
CN 203388271U, Electronic cigarette, (Year: 2014).*
International Search Report from International Application No. PCT/CN2020/121010 mailed Jan. 14, 2021.
Written Opinion of the International Searching Authority for International Application No. PCT/CN2020/121010 dated Jan. 14, 2021 with English translation.
Extended European Search Report for European Application No. 20876836.6 mailed Oct. 20, 2022.
Communication Pursuant to Article 94(3) EPC for European Application No. 20876836.6 mailed May 8, 2024.
First Office Action for Chinese Application No. 201910996274.3 mailed Jul. 10, 2024.

* cited by examiner

ELECTRONIC ATOMIZATION DEVICE AND ATOMIZER THEREOF

CROSS-REFERENCE TO RELATED APPLICATIONS

This application is a U.S. National Stage of PCT/CN2020/121010 filed on Oct. 15, 2020, which claims priority to Chinese Patent Application No. 2019109962743, filed on Oct. 18, 2019, the entire contents of each of which are incorporated herein by reference in its entirety for all purposes.

TECHNICAL FIELD

The present disclosure relates to atomizers, in particular to an electronic atomizing device and an atomizer thereof.

BACKGROUND

During the use of electronic atomizing devices in the fields of medical treatment or electronic cigarettes, as the use time increases, the atomizing core is prone to age, and it is easy to result in defects such as low atomizing efficiency or the generation of some harmful substances. Accordingly, an electronic atomizing device with a replaceable atomizing core has been developed in the industry to deal with this defect. The replaceable atomizing core assembly in the related art generally includes a fixing tube for accommodating and fixing the internal heating assembly and a connecting tube located outside the fixing tube. The fixing tube is generally fixed into the connecting tube by riveting. The connecting tube is provided with a thread and other structures on the outside thereof for connecting and fixing with the liquid storage assembly. This method solves the aforementioned defects to a certain extent, but the atomizing core assembly in this solution often requires twisting operations during assembly and disassembly, which is inconvenient to operate and increases the difficulty of structural design.

SUMMARY

An electronic atomizing device and an atomizer thereof are provided according to various embodiments of the present disclosure.

An atomizer includes a liquid storage assembly and an atomizing assembly. The liquid storage assembly forms a liquid storage cavity therein and an accommodating cavity in communication with the liquid storage cavity, the accommodating cavity includes a first opening formed on a surface of the liquid storage assembly. The atomizing assembly is detachably embedded in the liquid storage assembly via the first opening and the atomizing assembly is accommodated in the accommodating cavity in an interference fit manner via at least one sealing member.

In some embodiments, the liquid storage assembly includes at least one first liquid inlet communicating the accommodating cavity and the liquid storage cavity, the liquid storage cavity is in fluid communication with the atomizing assembly via the at least one first liquid inlet.

In some embodiments, the liquid storage assembly includes an air inlet channel extending from top to bottom, and the air inlet channel has an air outlet of at a lower portion thereof in communication with the accommodating cavity.

In some embodiments, the liquid storage assembly includes an air outlet channel in communication with the top end of the accommodating cavity.

In some embodiments, the at least one sealing member includes a first sealing member and a second sealing member located between an inner surface of the accommodating cavity and an outer surface of the atomizing assembly, the first sealing member and the second sealing member are located on a upper side and a lower side of the at least one first liquid inlet, respectively.

In some embodiments, the atomizing assembly includes a base and an atomizing core assembly disposed on the base, and the atomizing core assembly has at least one second liquid inlet located between the first sealing member and the second sealing member, and the at least one second liquid inlet is in fluid communication with the at least one first liquid inlet.

In some embodiments, the base includes a first electrode connector and a second electrode connector that are insulated from each other, the atomizing core assembly includes a third electrode connector and a fourth electrode connector that are insulated from each other, the third electrode connector and the fourth electrode connector are in electrical contact with the first electrode connector and the second electrode connector, respectively.

In some embodiments, the base includes a seat and a fastening bracket connected to the seat, the fastening bracket has a second opening on a side thereof, and the atomizing core assembly is laterally mounted between the fastening bracket and the seat via the second opening.

In some embodiments, the seat is located in the first opening, the at least one sealing member further includes a third sealing member sleeved on a periphery of the seat.

In some embodiments, the seat has a disc shape, and has an accommodating groove circumferentially formed on an outer wall thereof and adjacent to a top surface thereof, the third sealing member is accommodated in the accommodating groove.

In some embodiments, a gripping groove is formed on the seat for pulling the atomizing assembly out of the liquid storage assembly, and an avoiding groove is provided at an edge of the first opening corresponding to the gripping groove.

In some embodiments, the seat and the fastening bracket are electrically conductive, and the base further includes a conductive column extended through the seat and insulated from the seat; the seat and the fastening bracket form the first electrode connector, and the conductive column forms the second electrode connector.

In some embodiments, a first insulating member is located between the seat and the conductive column, the seat has a central through hole to receive the first insulating member.

In some embodiments, the conductive column comprises an embedded portion located at a lower portion thereof and a conductive portion connected to the embedded portion and protruding from the top surface of the seat.

In some embodiments, the fastening bracket includes a blocking wall extending laterally, and the atomizing core assembly includes a flange abutting against with the blocking wall.

In some embodiments, the atomizing core assembly includes a conductive housing configured to form the third electrode connector and a conductive cylinder configured to form the fourth electrode connector; the conductive cylinder is provided in the conductive housing and insulated from the conductive housing, and the at least one second liquid inlet is formed on the conductive housing.

In some embodiments, the atomizing core assembly includes a fixing cylinder, a liquid absorbing member provided in the fixing cylinder, and a heating member provided in a central through hole of the liquid absorbing member.

An electronic atomizing device is further provided, which includes the aforementioned atomizer.

In some embodiments, the electronic atomizing device further includes a battery device, the atomizer is detachably mounted on the battery device, the battery device is configured to supply power to the atomizer.

In some embodiments, a receiving groove is formed on the top of the battery device, and the atomizer is detachably received in the receiving groove and is electrically connected to the battery device.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

It should be understood that the terms "front", "rear", "left", "right", "upper", "lower", "first", "second" and other terms are only for the convenience of describing the technical solutions of the present disclosure, rather than indicating that the device or element referred to must have special differences, so it cannot be understood as a limitation of the present disclosure. When an element is considered to be "connected" to another element, it can be directly connected to another element or indirectly connected to another element with a mediating element. Unless defined otherwise, all technical and scientific terms used herein have the same meaning as commonly understood by people who are skill in the art to which the present disclosure belongs. The terms used herein in the specification of the present disclosure is only for the purpose of describing specific embodiments, and is not intended to limit the present disclosure.

Figure 1:
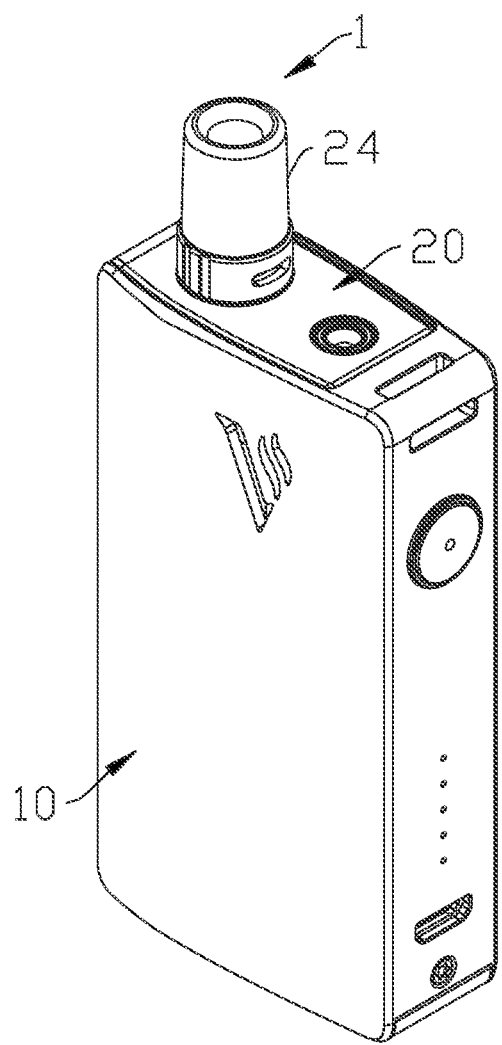
FIG. 1 is a perspective view of an electronic atomizing device according to some embodiments.
Figure 2:
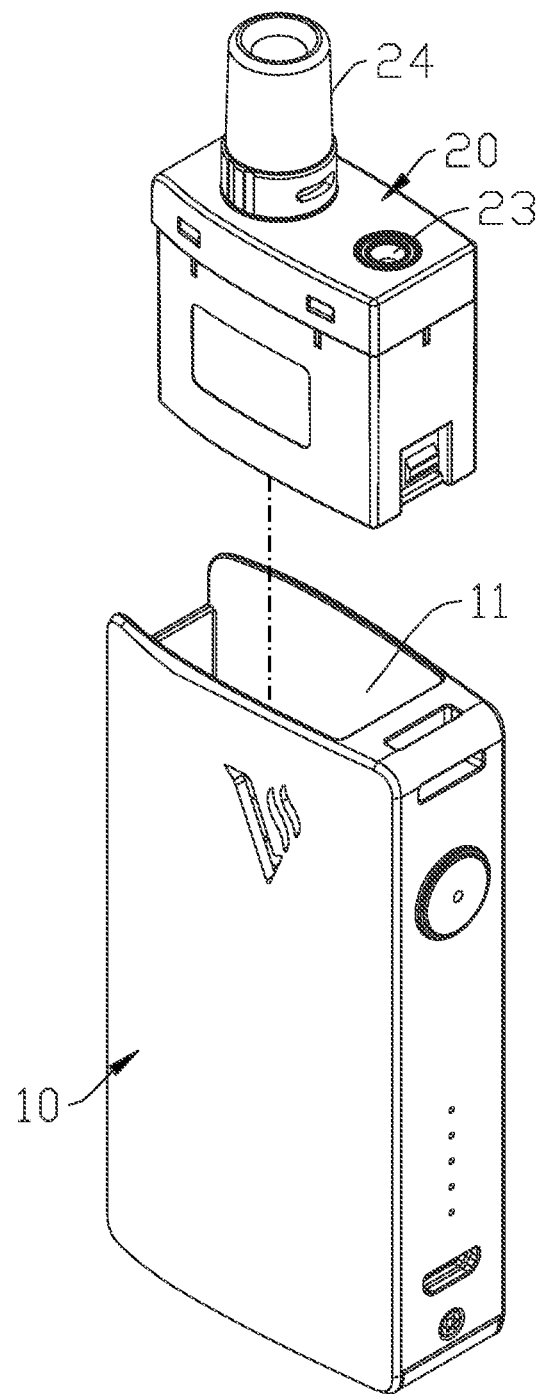
FIG. 2 is an exploded, perspective view of the electronic atomizing device shown in FIG. 1.

FIGS. 1 and 2 show an electronic atomizing device 1 according to some embodiments of the present disclosure. The electronic atomizing device 1 can be applied to heat and atomize liquid medium, such as tobacco liquid and liquid medicine. The electronic atomizing device 1 may include a battery device 10 and an atomizer 20 detachably mounted on the battery device 10. The battery device 10 is configured to supply power to the atomizer 20 and to control on/off of the atomizer 20. The atomizer 20 is configured to accommodate, heat, and atomize the liquid medium, and deliver the generated atomizing gas to a user. In some embodiments, a receiving groove 11 is formed on the top of the battery device 10, and the atomizer 20 is detachably received in the receiving groove 11 and is electrically connected to the battery device 10.

Figure 3:
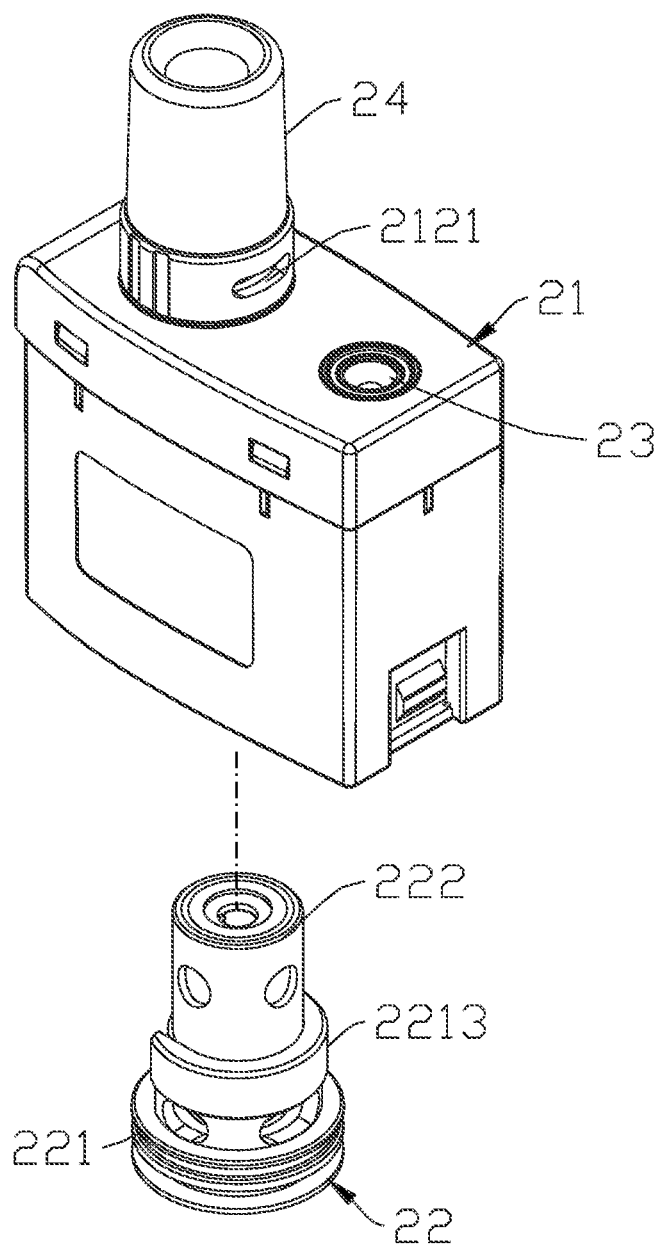
FIG. 3 is an exploded. perspective view of the atomizer shown in FIG. 2.
Figure 4:
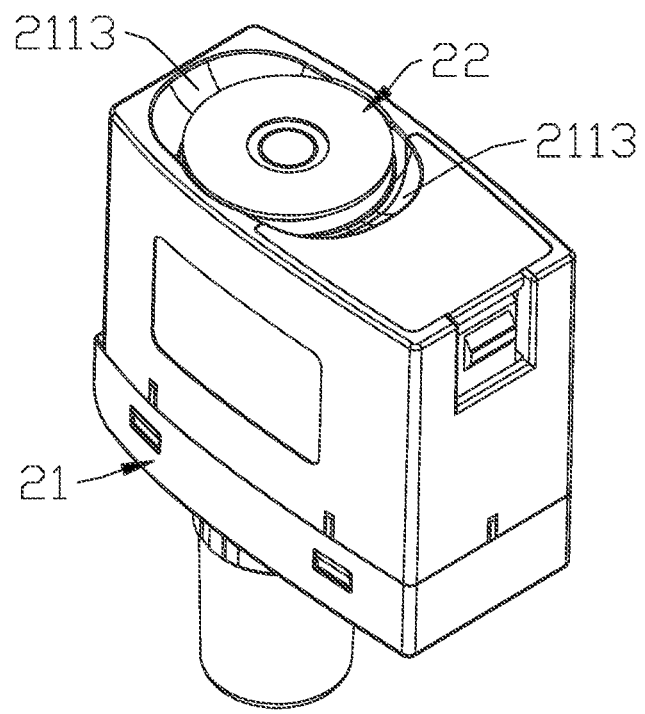
FIG. 4 is a perspective view of the atomizer shown in FIG. 2, but viewed from another aspect.
Figure 5:
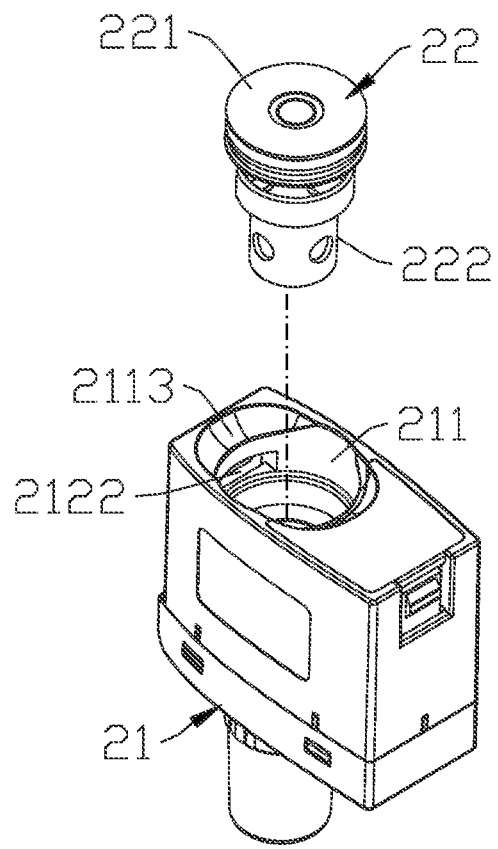
FIG. 5 is similar to FIG. 3, but viewed from another aspect.

Referring to FIGS. 3 to 5 together, in some embodiments, the atomizer 20 may include a substantially rectangular liquid storage assembly 21 and an atomizing assembly 22 detachably mounted in the liquid storage assembly 21. The liquid storage assembly 21 is mainly configured to store liquid medium. The atomizing assembly 22 is mainly configured to heat and atomize the liquid medium in the liquid storage assembly 21. In some embodiments, the atomizing assembly 22 can be inserted into the liquid storage assembly 21 in an interference fit manner, such that the atomizing assembly 22 is not easy to fall out of the liquid storage assembly 21, while maintaining a good sealing performance. This is even more effective in some cases that the atomizing assembly 22 does not have a cylinder shape.

In some embodiments, the atomizer 20 may further include a liquid injection device 23 and a mouthpiece assembly 24. The liquid injection device 23 is embedded on a top of the liquid storage assembly 21 and in communication with the liquid storage cavity 210 to facilitate liquid injection into a liquid storage cavity 210 of the liquid storage assembly 21. The mouthpiece assembly 24 is mounted on the top of the liquid storage assembly 21 and in communication with an air outlet channel 213 of the liquid storage assembly 21.

Figure 6:
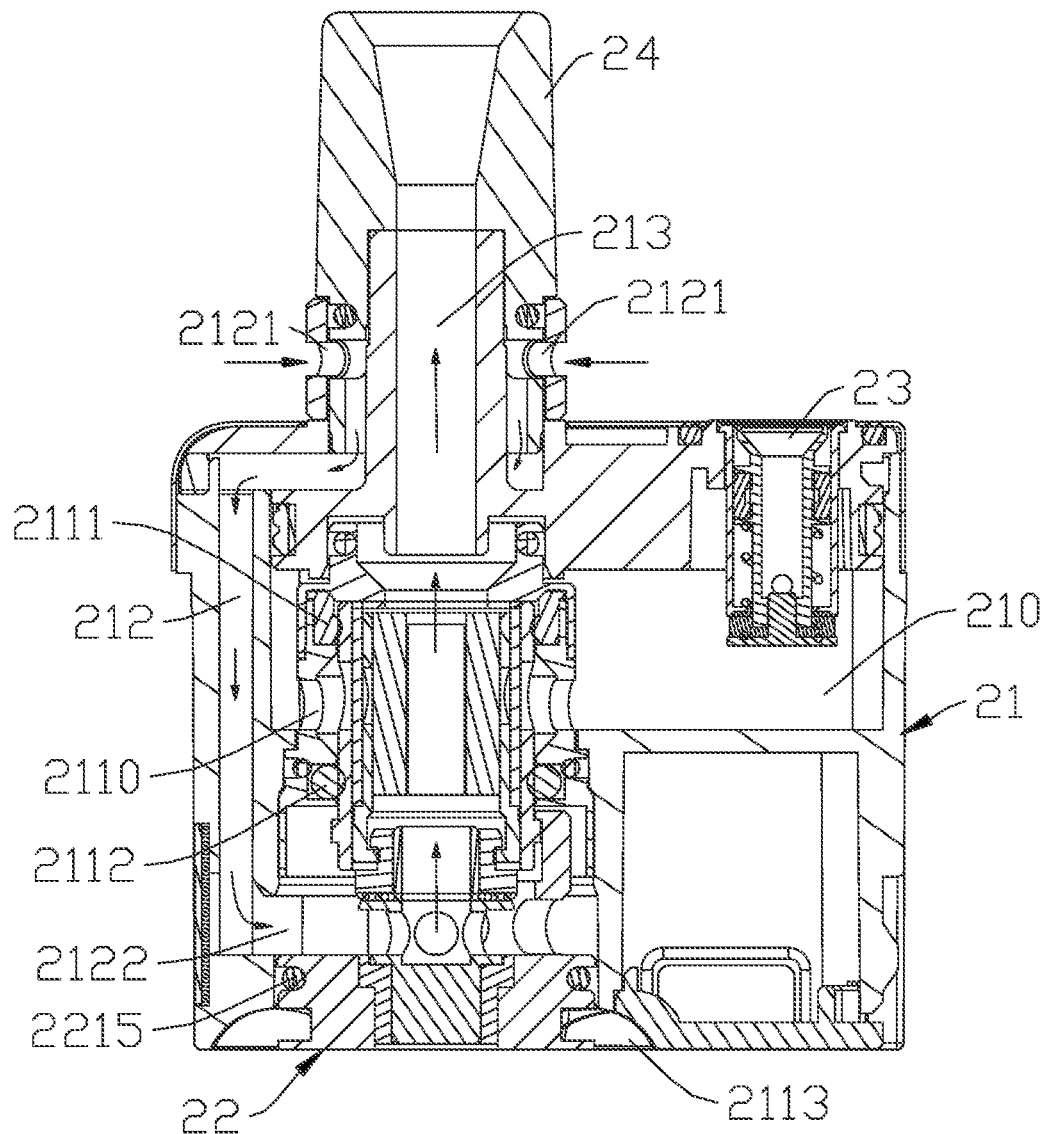
FIG. 6 is a longitudinal sectional view of the atomizer shown in FIG. 2.
Figure 7:
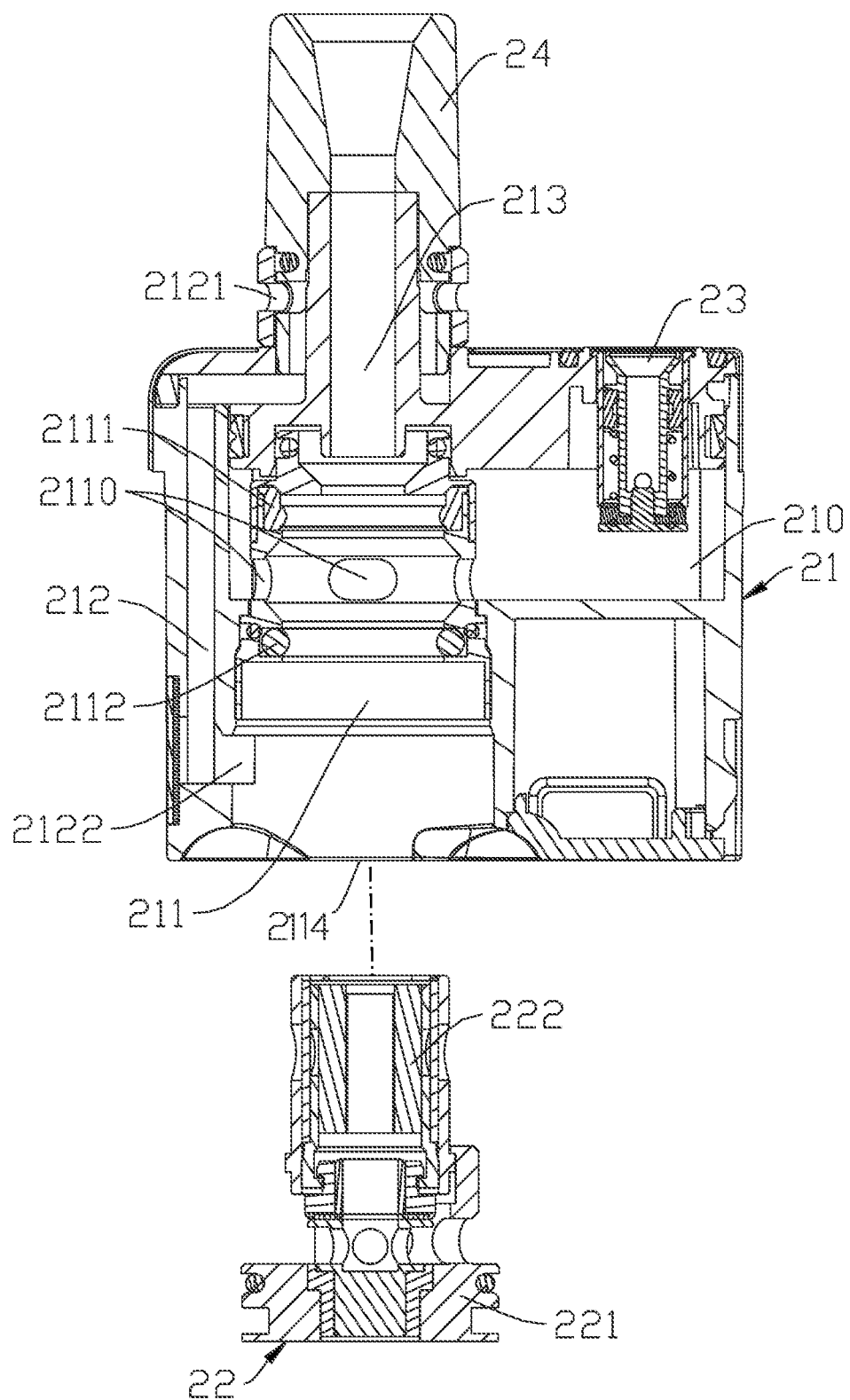
FIG. 7 is an exploded sectional view of the atomizer shown in FIG. 6.

Referring to FIG. 6 and FIG. 7 together, in some embodiments, the liquid storage assembly 21 may include the liquid storage cavity 210, an accommodating cavity 211 that is in fluid communication with the liquid storage cavity 210, an air inlet channel 212 in communication with a lower end of the accommodating cavity 211, and the air outlet channel 213 in communication with an upper end of the accommodating cavity 211. The liquid storage cavity 210 is configured to store liquid medium. In some embodiments, the accommodating cavity 211 may have a cylinder shape, and the atomizing assembly 22 with a cylinder shape can be detachably inserted in the accommodating cavity 211. The accommodating cavity 211 has a first opening 2114 formed on a lower surface of the liquid storage assembly 21. The accommodating cavity 211 extends vertically upward from the first opening 2114 into the liquid storage cavity 210, and the accommodating cavity 211 and the liquid storage cavity 210 are communicated with each other via a plurality of first liquid inlets 2110 that are uniformly formed around the accommodating cavity 211. The air inlet channel 212 extends from an air inlet 2121 on the mouthpiece assembly 24 to a lower portion of the liquid storage assembly 21, and the air inlet channel 212 is in communication with a lower portion of the accommodating cavity 211 via an air outlet 2122, such that air from outside can enter the liquid storage assembly 21 from the air inlet 2121, then flow downward and enter the atomizing assembly 22 from the air outlet 2122. The air outlet channel 213 is located right above the accommodating cavity 211 and in communication with a passage of the mouthpiece assembly 24, such that the atomized gas generated by the atomizing assembly 22 can be inhaled by the user from the mouthpiece assembly 24.

In some embodiments, the accommodating cavity 211 is provided with a first sealing member 2111 and a second sealing member 2112. The first sealing member 2111 and the second sealing member 2112 may be both O-rings, which are arranged at an upper side and a lower side of the first liquid inlet 2110, respectively. This configuration, on the one hand, allows the atomizing assembly 22 to be inserted into the accommodating cavity 211 in an interference fit manner, and on the other hand, the liquid medium can also be prevented from leaking during the process of entering the atomizing assembly 22 via the first liquid inlet 2110. The air outlet 2122 of the air inlet channel 212 is located below the second sealing member 2112, so as to isolate the air inlet channel 212 from the first liquid inlets 2110.

Figure 8:
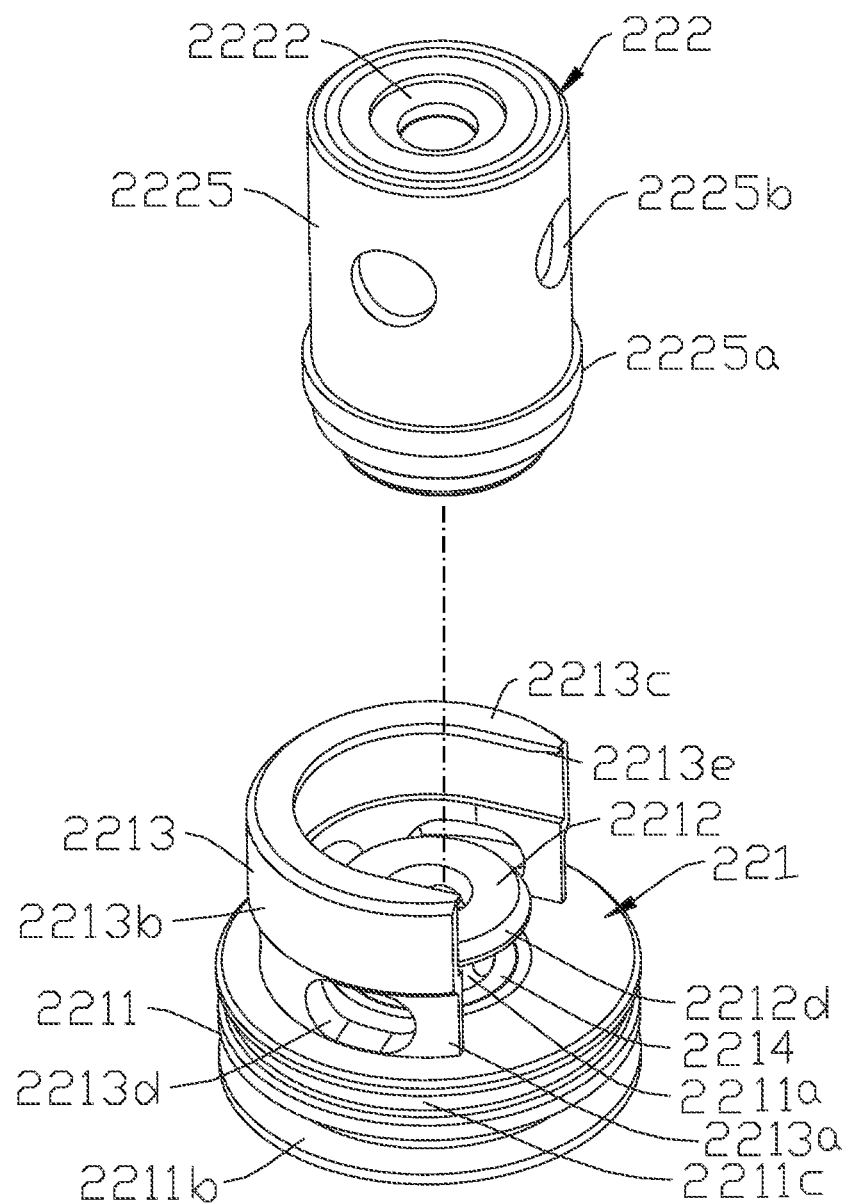
FIG. 8 is an exploded, perspective view of the atomizing assembly shown in FIG. 3.
Figure 9:
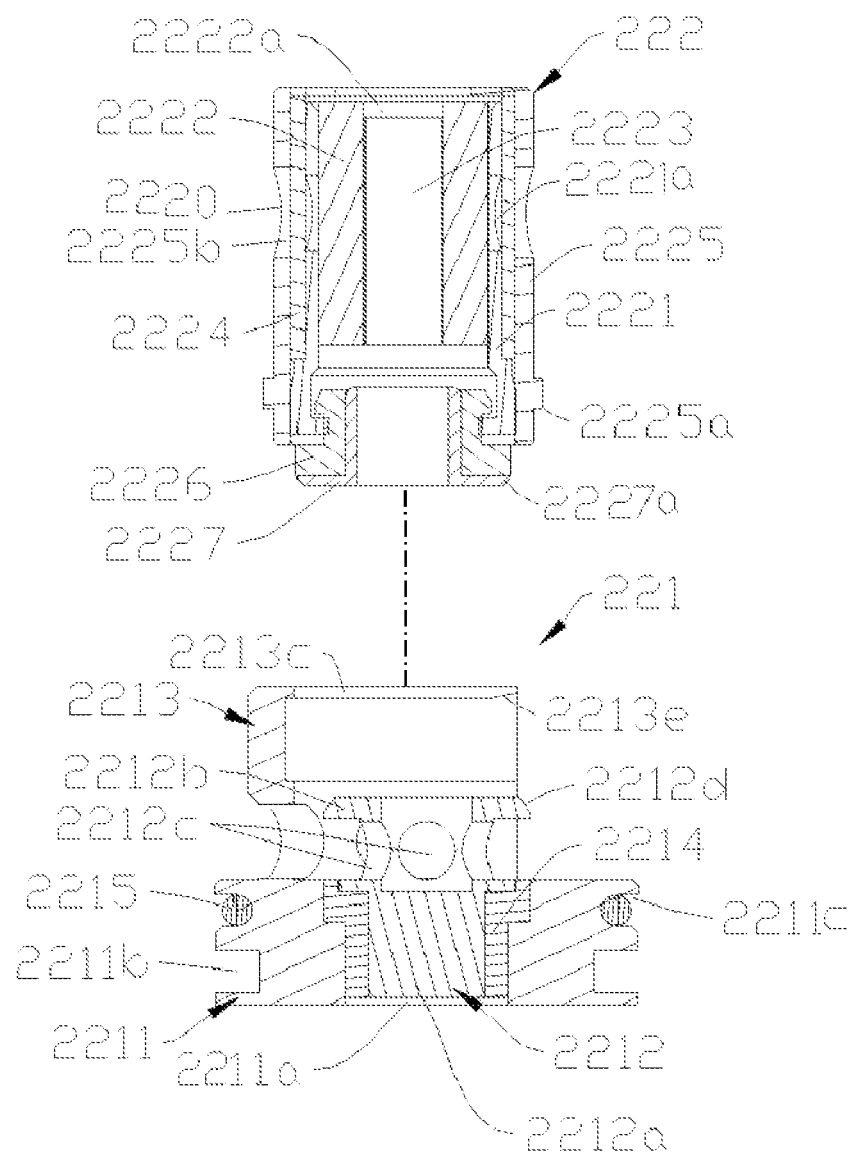
FIG. 9 is an exploded sectional view of the atomizing assembly shown in FIG. 3.

As shown in FIGS. 8 and 9, the atomizing assembly 22 is detachably embedded in the liquid storage assembly 21 via the first opening 2114. In some embodiments, the atomizing assembly 22 may include a base 221 and an atomizing core assembly 222 disposed on the base 221, such that the base 221 can be reused by replacing the atomizing core assembly 222. In some embodiments, the atomizing core assembly 222 is laterally mounted on the base 221 from one side of the base 221. The atomizing core assembly 222 has at least one second liquid inlet 2225b located between the first sealing member 2111 and the second sealing member 2112. The at least one second liquid inlet 2225b is in one-to one correspondence and in fluid communication with the at least one first liquid inlet 2110.

In some embodiments, the base 221 may include a conductive seat 2211 located in the first opening 2114, a conductive column 2212 extending through the seat 2211 and insulated from the seat 2211, and a fastening bracket 2213 integrally formed on the top of the seat 2211. The seat 2211 and the fastening bracket 2213 are used as the first electrode connector of the atomizing assembly 22, which is electrically connected to one of the positive electrode and the negative electrode of the battery device 10. The conductive column 2212 are used as the second electrode connector of the atomizing assembly 22, which is electrically connected to the other one of the positive electrode and the negative electrode of the battery device 10. The fastening bracket 2213 is configured to hold the atomizing core assembly 222 and electrically connect the atomizing core assembly 222 with the seat 2211. In some embodiments, a first insulating member 2214 is located between the seat 2211 and the conductive column 2212 to achieve an insulation. At the same time, the elastic characteristic of the first insulating member 2214 allows the conductive column 2212 to have a certain axial displacement after being subjected to an external force, so as to facilitate the mounting of the atomizing core assembly 222.

In some embodiments, the seat 2211 may have a disc shape, and have a central through hole 2211a to receive the first insulating member 2214. A gripping groove 2211b is formed on an outer surface of the seat 2211 in a circumferential direction adjacent to the bottom surface. The gripping groove 2211b is introduced for the user to conveniently grip the atomizing assembly 22 by fingers and pull the atomizing assembly 22 out of the liquid storage assembly 21. Correspondingly, an avoiding groove 2113 is provided at an edge of the first opening 2114 corresponding to the gripping groove 2211b, so as to facilitate user's operation. An accommodating groove 2211c is formed on the outer surface of the seat 2211 in a circumferential direction adjacent to a top surface. The accommodating groove 2211c is configured to accommodate a third sealing member 2215. On the one hand, the third sealing member 2215 can increase the friction force between a side surface of the atomizing assembly 22 and an inner surface of the accommodating cavity 211, and on the other hand, the third sealing member 2215 can prevent liquid from leaking through the gap between the side surface of the atomizing assembly 22 and the inner surface of the accommodating cavity 211. In the illustrated embodiment, the atomizing assembly 22 and the liquid storage assembly 21 are fitted together via three spaced apart sealing members 2111, 2112, 2215 which are located on an upper portion, a middle portion, and a lower portion respectively, thus the connection is very stable.

In some embodiments, the conductive column 2212 may include a solid cylindrical embedded portion 2212a located at a lower portion thereof and a cylindrical conductive portion 2212b connected to the embedded portion 2212 and protruding from the top surface of the seat 2211. The conductive portion 2212b is provided with a plurality of air inlet holes 2212c at a sidewall thereof, such that a central through hole of the conductive portion 2212b can be in communication with an outside environment. The cylindrical conductive portion 2212b has a head portion with a larger diameter, and an upper edge of the head portion is also provided with a chamfered first guiding portion 2212d to facilitate the mounting of the atomizing core assembly 222 to the base 221.

In some embodiments, the fastening bracket 2213 may be C-shaped with an opening, and the atomizing core assembly 222 can be mounted in the fastening bracket 2213 from the opening thereof. The fastening bracket 2213 may include a C-shaped connecting wall 2213a connected to the seat 2211, a C-shaped fixing wall 2213b connected to an upper side of the connecting wall 2213a, and a plane C-shaped blocking wall 2213c connected to an upper side of the C-shaped fixing wall 2213b and turned horizontally inward. A plurality of air holes 2213d can be formed on the connecting wall 2213a to facilitate the air to flow smoothly. The blocking wall 2213c is configured to position the atomizing core assembly 222 in an axial direction, and the blocking wall 2213c may also be provided with a second guiding portion 2213e at a lower surface of the end thereof adjacent to an opening of the fastening bracket 2213, such that the atomizing core assembly 222 can be easily latched into the fastening bracket 2213 from a lateral direction.

As shown in FIGS. 8 and 9, in some embodiments, the atomizing core assembly 222 may include a conductive fixing cylinder 2221, a cylindrical liquid absorbing member 2222 provided in the fixing cylinder 2221, a heating member 2223 provided in a central through hole of the liquid absorbing member 2222, a liquid filtering member 2224 surrounding the fixing cylinder 2221, a cylindrical conductive housing 2225 surrounding the liquid filtering member 2224 and being electrically connected to the fixing cylinder 2221, a second insulating member 2226 mounted at a lower end of the fixing cylinder 2221, and a conductive cylinder 2227 extending through the second insulating member 2226. The central through hole of the liquid absorbing member 2222 defines an atomizing cavity 2222a, and the conductive cylinder 2227 is in communication with the atomizing cavity 2222a. A third guiding portion 2227a is formed on an outer edge of the lower end of the conductive cylinder 2227 to cooperate with the first guiding portion 2212d of the conductive column 2212 to facilitate the mounting of the atomizing core assembly 222. In some embodiments, the liquid absorbing member 2222 can be made of cotton. The heating member 2223 may be a heating wire or a heating mesh.

The heating member 2223 includes two terminals (not shown) which are electrically connected to the fixing cylinder 2221 and the conductive cylinder 2227, respectively. The fixing cylinder 2221 and the conductive cylinder 2227 are electrically connected to the seat 2211 and the conductive column 2212, respectively, and then are electrically connected to the positive electrode and the negative electrode of the battery device 20, respectively. In the illustrated embodiment, the fixing cylinder 2221 and the conductive cylinder 2227 are configured as a third electrode connector and a fourth electrode connector of the atomizing assembly 22. The liquid filtering member 2224 is configured to prevent excessive liquid flowing into the liquid absorbing member 2222, which results in insufficient atomizing.

The plurality of second liquid inlets 2225b are formed on the conductive housing 2225. In some embodiments, the fixing cylinder 2221 includes a third liquid inlet 2221a corresponding to the second liquid inlets 2225b, such that the liquid from the liquid filtering member 2224 can reach the liquid suction member 2222 via the third liquid inlet 2221a. In some embodiments, the conductive housing 2225 may include an annular flange 2225a formed on an outer surface of the conductive housing 2225 adjacent to a lower end thereof. The flange 2225a can abut against the blocking wall 2213c of the fastening bracket 2213, so as to achieve a longitudinal positioning of the atomizing core assembly 222.

When assembling the atomizing assembly 22, a lower end of the atomizing core assembly 222 is firstly aligned with the lateral opening of the fastening bracket 2213 of the base 221, so that the flange 2225a of the conductive housing 2225 corresponds to a second guiding portion 2213e of the blocking wall 2213c of the fastening bracket 2213, and the third guiding portion 2227a of the conductive cylinder 2227 corresponds to the first guiding portion 2212d of the conductive column 2212. In the embodiment, both the first insulating member 2214 and the second insulating member 2226 are made of soft material. Then, the soft first insulating member 2214 and second insulating member 2226 are slightly elastically deformed by applying a lateral pressure, such that the conductive cylinder 2227 and the conductive column 2212 move away from each other, and the lower end of the atomizing core assembly 222 can be completely pushed into the fastening bracket 2213. When the atomizing assembly 22 is assembled, the conductive cylinder 2227 is in contact with the conductive column 2212, and the flange 2225a of the conductive housing 2225 abuts tightly against the blocking wall 2213c of the fastening bracket 2213. When the atomizing assembly 22 needs to be disassembled, an opposite lateral force is applied to overcome the friction force between the atomizing core assembly 222 and the base 221 to complete the disassembly.

Referring to FIG. 6 again, when the atomizing assembly 22 is to be assembled on the liquid storage assembly 21, the atomizing assembly 22 can be inserted into the accommodating cavity 211 from the first opening 2114 by an external force. At that time, the first sealing member 2111 and the second sealing member 2112 are engaged with the outer surface of the conductive housing 2225 in an interference fit manner, respectively. Since the first sealing member 2111 and the second sealing member 2112 are located on the upper side and the lower side of the second liquid inlet 2225b, the liquid storage cavity 210 can be in fluid communication with the accommodating cavity 211 via the second liquid inlets 2225b. The third sealing member 2215 is engaged with an inner sidewall of the accommodating cavity 211 adjacent to the first opening 2114 in an interference fit manner, and the third sealing member 2215 is located below the air outlet 2122, such that the air inlet channel 212 can be in communication with the air inlet hole 2212c of the conductive column 2212. The atomizing cavity 2222a of the atomizing core assembly 222 is in communication with the air outlet channel 213 of the liquid storage assembly 21, thereby completing the assembly of the atomizer 20 (the arrow in FIG. 6 shows the airflow direction). In some embodiments, after the atomizing assembly 22 is assembled to the liquid storage assembly 21, a bottom surface of the atomizing assembly 22 and the bottom surface of the liquid storage assembly 21 are coplanar, such that the atomizer 20 has a smooth bottom surface and a more compact structure.

While the disclosed subject matter has been described with reference to illustrative embodiments, this description is not intended to be construed in a limiting sense. Various modifications of the illustrative embodiments, as well as other embodiments of the subject matter, which are apparent to persons skilled in the art to which the disclosed subject matter pertains are deemed to lie within the scope of the disclosed subject matter.

What is claimed is:

1. An atomizer, comprising:
a liquid storage assembly forming a liquid storage cavity therein and an accommodating cavity in communication with the liquid storage cavity, the accommodating cavity comprising a first opening formed on a surface of the liquid storage assembly, the liquid storage assembly comprising an air outlet channel in communication with a top end of the accommodating cavity; and
an atomizing assembly detachably embedded in the liquid storage assembly along an axis direction of the air outlet channel via the first opening, and the atomizing assembly being accommodated in the accommodating cavity in an interference fit manner via at least one sealing member,
wherein the liquid storage assembly comprises at least one first liquid inlet communicating the accommodating cavity and the liquid storage cavity, the liquid storage cavity is in fluid communication with the atomizing assembly via the at least one first liquid inlet;
wherein the at least one sealing member comprises a first sealing member and a second sealing member located along the axis direction between an inner surface of the accommodating cavity and an outer surface of the atomizing assembly when the atomizing assembly is detachably embedded in the liquid storage assembly with the at least one liquid inlet positioned between and spaced from the first sealing member and the second sealing member.

2. The atomizer according to claim 1, wherein the liquid storage assembly comprises an air inlet channel extending from top to bottom, and the air inlet channel has an air outlet at a lower portion thereof in communication with the accommodating cavity.

3. The atomizer according to claim 2, wherein the liquid storage assembly comprises an air outlet channel in communication with a top end of the accommodating cavity.

4. The atomizer according to claim 1, wherein the atomizing assembly comprises a fixing cylinder, a liquid absorbing member provided in the fixing cylinder, and a heating member provided in a central through hole of the liquid absorbing member.

5. The atomizer according to claim 1, wherein the atomizing assembly comprises a base and an atomizing core assembly disposed on the base, the atomizing core assembly has at least one second liquid inlet located between the first sealing member and the second sealing member.

6. The atomizer according to claim 5, wherein the base comprises a first electrode connector and a second electrode connector that are insulated from each other, the atomizing core assembly comprises a third electrode connector and a fourth electrode connector that are insulated from each other, the third electrode connector and the fourth electrode connector are in electrical contact with the first electrode connector and the second electrode connector, respectively.

7. The atomizer according to claim 6, wherein the base comprises a seat and a fastening bracket connected to the seat, and the fastening bracket has a second opening on a side thereof, and the atomizing core assembly is laterally mounted between the fastening bracket and the seat via the second opening.

8. The atomizer of claim 7, wherein the seat is located in the first opening, the at least one sealing member further comprises a third sealing member sleeved on a periphery of the seat.

9. The atomizer of claim 8, wherein the seat has a disc shape and has an accommodating groove circumferentially formed on an outer wall thereof and adjacent to a top surface thereof, the third sealing member is accommodated in the accommodating groove.

10. The atomizer according to claim 9, wherein a gripping groove is formed on the seat for pulling the atomizing assembly out of the liquid storage assembly, and an avoiding groove is provided at an edge of the first opening corresponding to the gripping groove.

11. The atomizer according to claim 10, wherein the atomizing core assembly comprises a conductive housing configured to form the third electrode connector and a conductive cylinder configured to form the fourth electrode connector; the conductive cylinder is provided in the conductive housing and insulated from the conductive housing, and the at least one second liquid inlet is formed on the conductive housing.

12. The atomizer according to claim 7, wherein the seat and the fastening bracket are electrically conductive, and the base further comprises a conductive column extending through the seat and insulated from the seat; the seat and the fastening bracket form the first electrode connector, and the conductive column forms the second electrode connector.

13. The atomizer according to claim 12, wherein a first insulating member is located between the seat and the conductive column, the seat has a central through hole to receive the first insulating member.

14. The atomizer according to claim 13, wherein the conductive column comprises an embedded portion located at a lower portion thereof and a conductive portion connected to the embedded portion and protruding from the top surface of the seat.

15. The atomizer according to claim 13, wherein the fastening bracket comprises a blocking wall extending laterally, and the atomizing core assembly comprises a flange abutting against the blocking wall.

16. An electronic atomizing device comprising the atomizer according to claim 1.

17. The electronic atomizing device according to claim 16, further comprising a battery device, the atomizer being detachably mounted on the battery device, the battery device being configured to supply power to the atomizer.

18. The electronic atomizing device according to claim 17, wherein a receiving groove is formed on the top of the battery device, and the atomizer is detachably received in the receiving groove and is electrically connected to the battery device.

* * * * *